United States Patent [19]

Hermann, Jr. et al.

[11] Patent Number: 5,043,082
[45] Date of Patent: Aug. 27, 1991

[54] COLLECTION DEVICE AND METHOD OF USE THEREOF FOR THE CONCENTRATION, TRANSPORT AND PROCESSING OF CELLULAR COMPONENTS TO DETERMINE THE PRESENCE OR ABSENCE OF BIOMARKERS

[76] Inventors: William J. Hermann, Jr., 103 River Ridge Rd., Sealy, Tex. 77474; Tod S. Johnson, 8058 El Rio, Houston, Tex. 77054

[21] Appl. No.: 284,617

[22] Filed: Dec. 15, 1988

[51] Int. Cl.⁵ .................... B01D 37/00; B01D 29/085
[52] U.S. Cl. .................... 210/772; 210/451; 210/455; 210/477; 422/69; 422/101; 422/102; 436/18; 436/177
[58] Field of Search .............. 422/69, 70, 101, 102; 436/18, 177, 178; 210/651, 772, 321.6, 321.84, 455, 473, 477, 451

[56] References Cited

U.S. PATENT DOCUMENTS

| | | | |
|---|---|---|---|
| 3,882,026 | 5/1975 | McPhee | 210/451 |
| 4,301,010 | 11/1981 | Eddleman et al. | 210/455 |
| 4,393,141 | 7/1983 | Schlueter et al. | 436/178 |
| 4,557,902 | 12/1985 | Mussmann | 210/455 |
| 4,767,602 | 8/1988 | Johnson | 436/177 |
| 4,769,145 | 9/1988 | Nakajima | 210/451 |
| 4,806,487 | 2/1989 | Akers et al. | 436/178 |

Primary Examiner—W. Gary Jones
Attorney, Agent, or Firm—Jack W. Hayden

[57] ABSTRACT

A container having a longitudinal passage is provided with a filter for collecting thereon cellular components having a particle size range of 5 microns or greater. Where the cellular components are to be harvested from a hostile environment such as voided urine specimen, the hostile environment is discharged, after passing through the filter, from the container through one end thereof to separate the cells from the hostile environment as soon as possible. The cellular components harvested on the filter are washed with a suitable media such as a saline solution and a nutrient preservative media, or fixative, such as by way of example formaldehyde is added to the container to assist in stabilizing the harvested cellular components on the filter. Where the cellular components are harvested from a hostile environment, a suitable closure may be added to one end of the container to close off the longitudinal passage before the preserving media is added. A closure is provided to seal off the collected cellular components in the container before transport.

5 Claims, 1 Drawing Sheet

U.S. Patent
Aug. 27, 1991
5,043,082
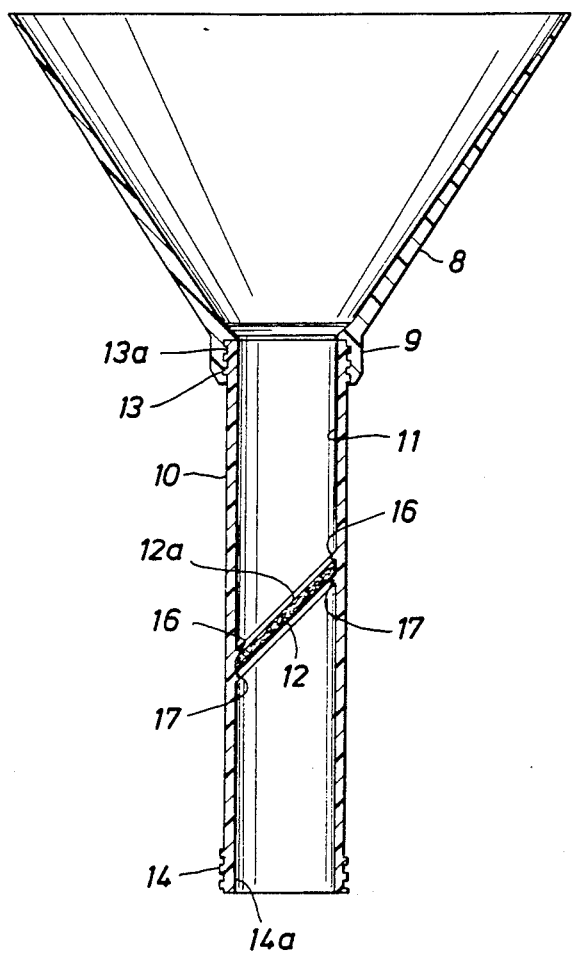
FIG. 1
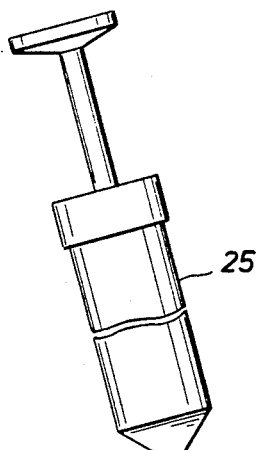
FIG. 2
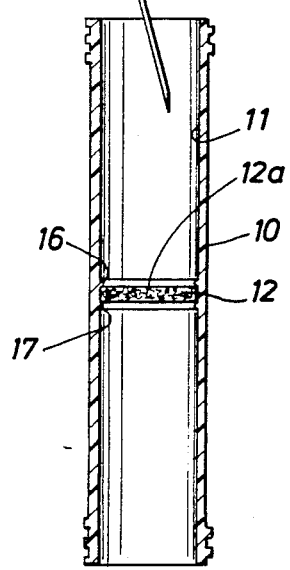
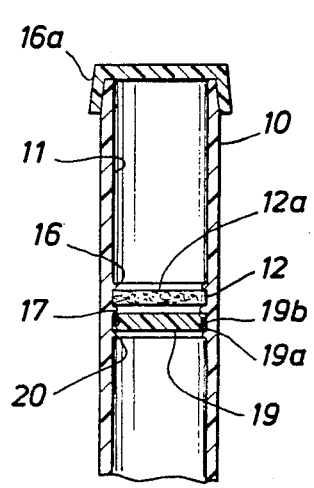
FIG. 3
FIG. 4
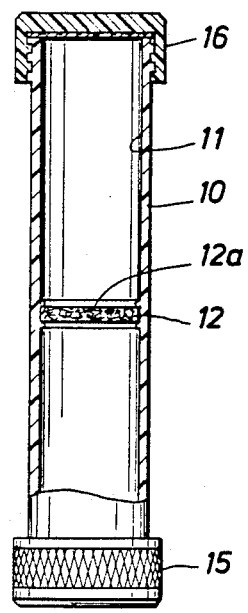

COLLECTION DEVICE AND METHOD OF USE THEREOF FOR THE CONCENTRATION, TRANSPORT AND PROCESSING OF CELLULAR COMPONENTS TO DETERMINE THE PRESENCE OR ABSENCE OF BIOMARKERS

STATEMENT OF THE PRIOR ART

The use of urine specimens for analysis is well known. The mass screening of urine for malignant cells; however, has only recently become practical and widely used due to instrument advancements involving laser and computer technology. It is desirable to collect the urine specimen and harvest the cells which are to be analyzed from the urine specimen in a gentle manner so as not to destroy, disrupt or otherwise effect the cell structure which in turn may have deleterious affects upon subsequent analysis of the cells. It is also desirable to concentrate the urine specimen before analysis to concentrate the number of cells and this concentration has heretofore been effected by centrifugation to reduce the volume of the urine specimen and in such process the cells may be destroyed, disrupted or otherwise adversely affected so far as further analysis is concerned.

While a voided urine specimen is one of the most convenient specimens available for analysis of cells or cellular components, such specimens are not always really practical or acceptable for analysis for a number of reasons.

For example, heretofore, urine samples have been collected in closed bottom containers, thus limiting or restricting the volume of the urine sample and hence the number of cells that may be collected in each sample.

Since, the urine samples generally contain too few cells per conveniently analyzable or transportable volume, concentration is desired or required before analysis or transport of urine specimen for analysis which, under present procedure as above noted, may adversely affect cell structure and hence the resulting analysis. Also, cell lysis begins within 30 minutes of collection due to destructive, lytic substances in the urine and therefore the cellular components must be separated from the hostile environment of the urine specimen as soon as possible and preferably immediately after collection. Even in those instances where desired cellular components are not present in a hostile environment, but are collected by fine needle aspiration, there is a substantial need for suitable means of collecting and preserving the cellular components to contain them in a proper environment and condition during transport and possible subsequent storage prior to analysis.

Heretofore in analysis for cancer of the bladder cell specimens from the bladder have been obtained by injecting a catheter into the bladder and discharging a saline solution to knock the cells off the wall of the bladder. Such procedure not only requires hospitalization and anesthesia to eliminate the pain during the cell collection, it also has the deleterious effect of possibly destroying, or disrupting the cells which again may effect the cell analysis.

A flow cytometer for analysis has the advantage that it can look at millions of cells to see if even a small percentage are malignant. The above described methods of cell collection are thus disadvantageous or impractical for analysis by a flow cytometer.

It is desirable, if not necessary, that a mass volume of cells be harvested in a manner to overcome the problems above mentioned as well as others.

It is also desirable that the laboratory processing and analysis of cellular components be done as expeditiously as possible with a minimum volume of treating, handling or testing reagents to maintain the cell analysis at a minimum cost to the patient.

Quite often the laboratory which conducts the analysis may be a substantial distance from the point of collection and substantial delay is therefore involved before cell analysis occurs. It is desired to maintain the harvested cellular components in a state or condition to avoid deterioration which may lead to incorrect analysis, or prevent analysis and so as to not interfere with subsequent processing for instrument analysis or other type analysis in the same container.

SUMMARY OF THE PRESENT INVENTION

The present invention provides an apparatus and method for enabling an unlimited volume of a voided urine specimen to pass through a cell collection device from which a large number of cells may be harvested in a manner to overcome the above and other problems.

The present invention includes a container which may, if desired, include a funnel to which the container is removably connected. The container is sized to accommodate transport and is open ended so that a large volume of urine may be passed therethrough to harvest a maximum number cells. Thus, the present invention provides a method and collection device whereby a large volume of desired cellular components in a hostile environment may be harvested and separated from the hostile environment, the hostile environment discharged from the container and thereafter the harvested cells washed with a suitable media such as a saline solution and the container closed at one end for receiving a preserving and/or nutrient media therein to keep the cells alive whereupon the other end of the container may be closed.

Another object of the present invention is to provide a sample container of relative simple construction which enables a large volume of voided urine to be passed therethrough so that a large volume of cells may be harvested therefrom on a suitable filter in the specimen collection apparatus. The cells can then be washed to remove the urine from the harvested cells and a preserving and/or nutrient media then injected into the specimen collector and the specimen collector closed for transport. When the specimen container is received at the lab, the specimen can be washed in the same container with saline solution to remove the preservative or nutrient media and then a non-porous membrane inserted into the container immediately beneath the filter to reduce substantially the volume of a reagent required for staining the cells collected on the filter.

By retaining the specimen in the same container during the treatment steps at the laboratory the cost of the analysis is reduced since the specimen need not be changed from one container to another as is generally required with prior methods of cell collection and transport. If the cells are not to be immediately analyzed, the container with suitable cell stabilizing media therein may be closed, or capped for later analysis. This substantially increases the rate of lab processing, further helping to reduce cost of the analysis by enabling more rapid analysis of specimen samples by reducing the steps required that would otherwise be present if the cells were transferred from one container to another container as is normally required with present general analysis.

The present invention allows the harvesting and collection of cells in a gentle manner from a large volume of voided urine to obtain a large volume of cells, their immediate removal from a hostile environment, by washing with a solution, and enclosing them with a nutrient/preservative solution all in the same collection device. Also the expensive and painful bladder collection method above referred to is eliminated.

The present invention also enables cells to be readily collected at remote locations without hospitalization such as industrial sites as, for example, chemical plants where bladder cancer may be more prevalent by providing a method and means where a larger urine specimen may be employed from which more cells are harvested in a proper manner, removed from the hostile environment of the urine and preserved immediately to inhibit cell deterioration.

In another form of the invention, the container includes a non-porous membrane formed of plastic or other suitable material extending across the longitudinal passage in the container and in spaced relation to the filter that extends across the longitudinal passage for closing off one end of the container passage whereby chemical antibody reagents may be discharged into the container for laboratory processing.

BRIEF DESCRIPTION OF THE DRAWINGS

FIGS. 1-4 are cross sectional views of embodiments of the invention.

DESCRIPTION OF THE PREFERRED EMBODIMENTS

Attention is first directed to FIG. 1 of the drawings wherein a funnel formed of any suitable material such as plastic or the like is represented by the numeral 8 and is shown as having threadedly connected at its lower open end 9 a longitudinal container 10 having a passage 11 therethrough. This connection may be a luer lock, friction connection or any other suitable connector means. The container 10 may be connected with the funnel means 8 by any suitable means such as, by way of example only, threads 13 on one end for engaging with threads 13a on the funnel. The container 10 may be provided with any suitable means, such as threads 14 at its other end whereby closures or caps 15 and 16 may be applied at each end of the container 10. It can be appreciated that any suitable form of closure such as stoppers, or other removable means such as friction engaging means at each end of the container 10 may be employed to seal off the container contents when desired may be employed.

Extending across the longitudinal passage 11 is a filter 12 for harvesting and collecting cellular components thereon.

Where the cellular components are present in a hostile environment such as by way of example only, urine, it is preferable that the cells be separated from the hostile environment as soon as possible to maintain them suitable for analysis. In order to obtain a larger concentration or volume or number of cells per unit size of sample, the funnel 8 may be employed so that the urine can be discharged directly into the container 10 and flowed through the filter 12 and out the open lower end 14a. The filter 12 will preferably have a pore size so as to filter and harvest cellular components on the top surface 12a thereof within the particle size range of about 5 microns or greater. After the hostile environment is discharged out the lower open end represented at 14a on the container 10 a suitable washing media such as saline solution may be poured into the container and passed through the longitudinal passage 11 of the container 10 to wash the collected cellular components on the surface 12a of the filter 12.

Thereafter a closure such as represented at 15 in FIG. 3 may be secured with the lower end 14a of the container 10 and a suitable nutrient and/or preservative media such as tissue culture media, or fixative such as, by way of example only, formaldehyde, added to the container to preserve the collected cellular components during transport. A top 16 may be connected to the top open end of the container 10 to close it off and protect the cellular components during transport and storage.

It is to be noted that in FIG. 1 the filter 12 is shown as extending diagonally at an angle across the passage 11 whereas in FIGS. 2 and 3 the container 10 is shown as extending diametrically across the passage 11. Annular enlargements 16 and 17 on the inner wall of passage 11 are provided above and below the filter 12 for releasably retaining the filter in position in the longitudinal passage.

In FIG. 4 the top closure for the container 10 is shown as being shaped to conform with the upper end of the container 10 which upper end is provided with an inclined annular edge to frictionally engage and retain the cap 16a of suitable form as shown in FIG. 4 thereon.

Also in FIG. 4 a non-porous or solid membrane formed of suitable material such as plastic or the like is illustrated at 19 and is shown as extending across the inside of the longitudinal passage 11 and below filter 12. The non-porous membrane or solid member 19 is retained in position by enlargement 20 formed on the inner wall of the passage 11 on one side and where the membrane 19 is immediately adjacent the filter 12, the projection 17 in the passage 11 may be employed to assist in releasably retaining the membrane 19 in position. The membrane or solid member 19 includes an annular edge surface 19a, on which a suitable seal such as O-ring 19b is received in a suitable groove in edge 19a, to engage the inner wall of passage 11 and seal therewith.

The filter 12 may be inserted in the passage 11 and moved manually to position between the enlargements 16 and 17. Similarly, the membrane 19 may be inserted in the other end of passage 11 and positioned between enlargements 17 and 20. The retaining projections 16 and 17 for the filter and the retaining projections 17 and 20 for the membrane 19 which removably retain the filter 12 and membrane in position in the longitudinal passage 19 enable each the filter and/or membrane to be separately and quickly and readily removed and/or replaced when desired by displacing them from their retaining projections.

The container 10 connected with the funnel 8 may be of any suitable size and when the funnel is employed, it may approximate 250 milliliters in volume by way of example only. The inner diameter of the container 10 will be of sufficient size to promote rapid flow rate therethrough by way of example such as two centimeters in diameter. The length of the container 10 may be of any suitable size and in some instances may approximate a length of as much as 10 centimeters.

FIG. 2 illustrates collection of cellular components on the filter 12 by a syringe 25 which has been used to collect cellular components from any portion of the body. The cellular components and any fluid accidentally collected therewith in the syringe 12 by fine needle aspiration may be injected directly into the container 10 on the filter 12.

While collection of substances on filter is well known, one of the primary objects of the present invention is to use a large volume of sample and separate a large volume of cellular components from hostile environments, such as urine and the like almost immediately and to replace the hostile environment with a wash solution and then another solution to maintain the cells alive or preserve or fix them with a cytological fixative to maintain them in proper condition in a vessel of manageable size during transport and storage prior to analysis at a laboratory.

Another advantage of the present invention is that the collection container 10 can be used as a test vessel or as staining vessel for the cellular components if desired to avoid placing the cells in another vessel. This saves time and expense to the patient.

FIG. 4 illustrates a container where a non-porous membrane or member 19 is positioned immediately below the filter. Reagents used in analysis can be quite expensive and the container of FIG. 4 maintains the test reagent volume at a minimum.

In some instances, cellular components or cell suspensions may be very sparse and a substantially large volume is required to get enough cells for shipment and proper analysis. The present invention not only provides an apparatus for harvesting cellular components from a large volume, but it also provides a relatively simple arrangement for washing and preserving the cellular components for subsequent analysis, as well as enabling the steps involved in the analysis to be conducted in the collection container. This eliminates the prior procedure of removing the collected cells from the transport container to another container before analysis.

Carcinoma or cancer of the urinary bladder is a potentially curable disease if detected and treated early. However, when the carcinoma is advanced, it is a very difficult tumor to eradicate. The present apparatus and method provide an arrangement for readily obtaining available suitable specimens without pain to the patient from a large volume of hostile environment for harvesting and trapping the cells without retaining the hostile environment and to provide a maximum number of cells for a more accurate and quick analysis as well as a collection container that is manageable in size for transport.

At the present time, the most advanced instrumentation for cancer detection is available at only a limited number of laboratories and this requires that substantial transport requirements exist since proper diagnosis is substantially totally dependent on carefully collected and preserved, stabilized cellular components.

Minor modifications may be apparent to those skilled in the art without departing from the scope of the present invention.

The foregoing disclosure and description of the invention are illustrative and explanatory thereof, and various changes in size, shape and materials as well as in the details of the illustrated construction may be made without departing from the spirit of the invention.

What is claimed is:

1. Apparatus for harvesting and trapping cellular components from a volume of specimen conducted through a funnel like member, said apparatus comprising:
    a container having a longitudinal passage which is open at each end;
    means for removably connecting said container with the member to discharge the specimen through said longitudinal passage;
    a filter extending across said longitudinal passage to separate, trap and harvest cellular components from the specimen volume conducted through said longitudinal passage; and
    closures to close off communication through each open end of said longitudinal passage to trap and preserve the cellular components on the filter in said longitudinal passage of said container wherein one of said closures comprises a non-porous membrane removably supported in the longitudinal passage.

2. A method of harvesting and trapping cellular components from a hostile environment volume including the steps of:
    discharging the hostile environment volume having the cellular components into an open ended longitudinal passage in a container;
    conducting the hostile environment volume containing cellular components through a filter to harvest the cellular components thereon in the longitudinal passage and discharging the hostile environment volume from the open ended longitudinal passage to separate the hostile environment from the cellular components harvested on the filter as quickly as possible;
    washing the harvested cellular components on the filter to remove remaining hostile environment;
    closing one end of the longitudinal passage;
    adding a preservative and/or nutrient media to the container; and
    closing the other end of the open ended longitudinal passage.

3. A method of harvesting and trapping cellular components including the steps of:
    discharging the cellular components into a container having an open ended longitudinal passage and collecting them on a filter in the longitudinal passage;
    washing the collected cellular components; and
    conducting desired tests on the cellular components on the filter in the longitudinal passage.

4. The method of claim 3 wherein the testing comprises staining the cellular components in the longitudinal passage harvested on the filter.

5. Apparatus for harvesting and trapping cellular components from a volume of specimen for analysis by a reagent, said apparatus comprising:
    a container having a longitudinal passage with openings at each end for conducting the specimen therethrough;
    a filter extending across said longitudinal passage to separate and harvest thereon cellular components from the specimen volume for testing in the longitudinal passage of the container; and
    a non-porous membrane for removably positioning in the longitudinal passage adjacent said filter for maintaining the test volume of reagent to a minimum.

* * * * *